(12) United States Patent
Xia

(10) Patent No.: US 10,016,370 B2
(45) Date of Patent: Jul. 10, 2018

(54) COMPOSITION, DEVICE AND METHOD FOR DELAYED AND SUSTAINED RELEASE OF BRAIN ENERGY MOLECULES

(75) Inventor: Jun Xia, York, PA (US)

(73) Assignee: Able Cerebral, LLC, Ephrata, PA (US)

( * ) Notice: Subject to any disclaimer, the term of this patent is extended or adjusted under 35 U.S.C. 154(b) by 287 days.

(21) Appl. No.: 14/232,613

(22) PCT Filed: Jul. 13, 2012

(86) PCT No.: PCT/US2012/046782
§ 371 (c)(1),
(2), (4) Date: Jan. 13, 2014

(87) PCT Pub. No.: WO2013/010137
PCT Pub. Date: Jan. 17, 2013

(65) Prior Publication Data
US 2014/0180224 A1    Jun. 26, 2014

Related U.S. Application Data

(60) Provisional application No. 61/572,258, filed on Jul. 14, 2011.

(51) Int. Cl.
| | | |
|---|---|---|
| A61K 9/48 | (2006.01) | |
| A61K 31/7004 | (2006.01) | |
| A61K 9/28 | (2006.01) | |
| A61K 9/70 | (2006.01) | |
| A61K 31/19 | (2006.01) | |

(52) U.S. Cl.
CPC .......... *A61K 9/4891* (2013.01); *A61K 9/2846* (2013.01); *A61K 9/2866* (2013.01); *A61K 9/2886* (2013.01); *A61K 9/7084* (2013.01); *A61K 31/19* (2013.01); *A61K 31/7004* (2013.01)

(58) Field of Classification Search
None
See application file for complete search history.

(56) References Cited

U.S. PATENT DOCUMENTS

| | | | | |
|---|---|---|---|---|
| 4,695,464 A | * | 9/1987 | Alderman | A61K 9/0014 424/448 |
| 5,238,686 A | * | 8/1993 | Eichel | A61K 9/5073 424/461 |
| 5,238,933 A | * | 8/1993 | Catz | A61K 9/0014 514/236.2 |
| 6,056,977 A | * | 5/2000 | Bhagwat | A61K 9/2018 424/458 |
| 6,074,669 A | * | 6/2000 | Nagaprasad | A61K 9/2054 424/458 |
| 6,770,635 B1 | * | 8/2004 | Drube | A61K 31/7012 514/62 |
| 2002/0098242 A1 | * | 7/2002 | Darder | A61K 9/5078 424/490 |
| 2005/0084553 A1 | * | 4/2005 | Moon | A61K 8/97 424/773 |
| 2005/0096392 A1 | * | 5/2005 | Jager | A23L 1/293 514/554 |
| 2005/0186278 A1 | * | 8/2005 | Pierro Francesco | A61K 9/282 424/472 |
| 2005/0279377 A1 | * | 12/2005 | Sarjeant | A61C 15/041 132/321 |
| 2007/0212415 A1 | * | 9/2007 | Park | A61K 9/2077 424/468 |

FOREIGN PATENT DOCUMENTS

AU    2007200571    *    4/2008

OTHER PUBLICATIONS

Levina et al., The Influence of Excipients on Drug Release from Hydroxypropyl Methylcellulose Matrices, Journal of Pharmaceutical Sciences, vol. 93, No. 11, Nov. 2004 p. 2746-2754.*

* cited by examiner

*Primary Examiner* — Jennifer A Berrios
(74) *Attorney, Agent, or Firm* — Rodney J. Fuller; Booth Udall Fuller, PLC

(57) ABSTRACT

The present invention relates to compositions, devices and methods of delayed and sustained release of energy molecules for brain function to treat nocturnal hypoglycemia. The composition comprises an energy molecule required for human brain function; wherein the release of the energy molecule is delayed and then sustained over a period of time. The device is a transdermal delivery device comprising a reservoir layer containing the composition and a skin permeation enhancer formulation, an adhesive layer, a backing layer and a release liner. The method comprises administering the composition either orally or through the transdermal delivery device to a subject in need thereof immediately prior to going to sleep.

9 Claims, No Drawings

COMPOSITION, DEVICE AND METHOD FOR DELAYED AND SUSTAINED RELEASE OF BRAIN ENERGY MOLECULES

CROSS REFERENCE TO RELATED APPLICATIONS

This application is the U.S. National Stage of International Application No. PCT/US2012/046782, filed Jul. 13, 2012, which claims the benefit of the filing date of U.S. Provisional Patent Application No. 61/572,258 to Jun Xia entitled "Controlled Release of Brain Energy Molecules for Nocturnal Hypoglycemia" which was filed on Jul. 14, 2011; the disclosure of each of which is hereby incorporated herein by reference thereto in their entireties.

FIELD OF THE INVENTION

This invention relates to the delayed and controlled release of energy molecules useful for brain function. More particularly the invention relates to delayed and sustained release of glucose, mannose, lactic acid (lactate) and pyruvic acid (pyruvate) for brain energy supply via oral and transdermal formulations.

BACKGROUND OF THE INVENTION

Hypoglycemia, especially, nocturnal hypoglycemia, is not a well-managed disease. Even though hypoglycemic episodes may lead to impaired epinephrine response and diminished neurological function, patients ignore the disease due to the lack of a practical solution on the market and ignorance of the long-term impact on their health. Symptoms of nocturnal hypoglycemia are usually subtle and may include nightmares, morning fatigue, and headache. More serious symptoms, although rare, sometimes appear and include seizures and loss of consciousness.

Unrecognized hypoglycemic episodes are known to occur in 62.5% of type-1 diabetic patients and in 46.6% of type-2 diabetic patients, with the majority (73.7%) of all events occurring at night. It has been shown that a very high incidence of nocturnal asymptomatic hypoglycemic episodes occur in type-2 diabetic subjects treated with oral agents. Research has shown that most nocturnal hypoglycemic episodes happen around 4 am, and last longer than hypoglycemic episodes that occur at other times, with a medium duration of 3 hours.

Prominent products on the market, such as GLU-CERNA™ shakes or bars, claim to maintain glucose level for a maximum of 3 to 4 hours. Other efforts, such as U.S. Patent Application US2012/0015039, apply controlled-release technology for carbohydrates and other nutrients for sustainable delivery for only about 3 hours in order to enhance athletic performance, increase eye-hand coordination and maintain concentration on the task at hand. Similar efforts can be found in U.S. Pat. Nos. 7,943,163; 6,534,487; 5,576,306; 6,905,702; 6,316,427; 5,776,887; EP06747611; and WO2009/051786 which are hereby incorporated by reference.

U.S. Pat. No. 6,815,436 describes making granules of cornstarch for controlled enzymatic breakdown of amylose and amylopectin. Similarly, U.S. Pat. No. 6,316,427 describes using an uncooked cornstarch product for bedtime ingestion to slowly release carbohydrates. U.S. Pat. No. 5,776,887 describes a diabetic nutritional product for controlled absorption of carbohydrates by delivering "a rapidly absorbed fraction such as glucose or sucrose, a moderately absorbed fraction such as certain cooked starches or fructose, and a slowly absorbed fraction such as raw corn starch."

Controlled release of carbohydrates with initial release of sugars and lasting about 3-4 hours has been demonstrated. These efforts, however, come with unnecessary nutrients such as vitamins, minerals (such as sodium), and lipids which might have ill-effects for a sleeping individual. Additionally, the previous efforts have suggested delivering long-chain carbohydrates, which not only deliver an unpleasant fullness in the stomach, but also trigger digestion during sleep, and may disturb enzyme secretion thereby causing obesity in type-1 and -2 diabetes patients. A need exist for a composition that is effective at treating and managing hypoglycemia and especially without the side effects.

BRIEF SUMMARY OF THE INVENTION

The present invention is directed to a composition, method, and device for delayed and sustained release of energy molecules. One embodiment of the invention provides compositions to accurately manage nocturnal hypoglycemia. The composition preferably comprises one or more of the following brain energy molecules: glucose, mannose, lactic acid (lactate), and pyruvic acid (pyruvate). The four energy molecules most preferably delivered with this invention are utilized by the brain, especially of a human, for energy support. These four energy molecules do not require the human body to further digest during sleep. Thus, one embodiment of the composition prevents diabetes patients from further weight gain. The composition of the invention may include the energy molecules individually, or in combination of two, three, or four.

One embodiment of the invention includes delayed and sustained release of energy molecules which may provide patients taking tablets or capsules at bedtime to not be disturbed for their normal initial sleeping pattern. By delayed and sustained release of energy molecules for up to 8 hours, early morning hypoglycemia may be eliminated. The transdermal delivery device presented in this invention may provide the advantage of therapeutic management for early morning hypoglycemia. By applying the transdermal device near neck areas, the energy molecules typically directly penetrate into carotid arteries and are further transported to the central nervous system (CNS). Preferably, the transdermal delivery device of this invention also provides a near zero-order delivery of the energy molecules for a sustained period of at least 6-10 hours. One embodiment of the current invention allows patients to easily stop the energy molecule delivery by simply peeling off the device from their skin when they wake up in the morning.

One embodiment of the current invention provides a delayed and sustained release composition comprising an energy molecule required for human brain function; wherein less than 15% by weight of the energy molecule is released within 2 hours after administration, the energy molecule being released at a sustained rate after 2 hours, wherein less than 60% of the energy molecule is released within the first 4 hours of administration, and at least 80% of the energy molecule is released within 8 hours after administration.

A further embodiment provides wherein the energy molecule is selected from the group consisting of: glucose, mannose, lactic acid (lactate), and pyruvic acid (pyruvate). Lactic acid may be substituted for lactate, and pyruvic acid may be substituted for pyruvate.

A further embodiment provides a delayed and sustained release composition wherein the composition comprises a transdermal preparation, the preparation further comprising a skin permeation enhancer formulation comprising: at least one glycol selected from the group consisting of: propylene glycol, butylenes glycol, hexylene glycol, ethoxydiglycol, dipropylene glycol, and pentylene glycol; monothiogylcerol; at least one of 2-methyl-3-hydroxypyranone or 2-ethyl-3-hydroxypyranone; and an aliphatic carboxylic acid of 8 to 24 carbon atoms or an ester of an aliphatic carboxylic acid of 8 to 24 carbon atoms with an aliphatic alcohol of 1 to 14 carbon atoms and 1 to 2 hydroxy groups.

A further embodiment provides a delayed and sustained release composition wherein the composition is in an oral tablet or capsule form.

A further embodiment provides a delayed and sustained release composition wherein the amount of the energy molecule is between about 250 and about 1250 milligrams.

A further embodiment provides a delayed and sustained release composition comprising a coating of a pH-dependent polymer on the oral tablet.

A further embodiment provides a delayed and sustained release composition comprising a hydrophilic polymer.

A further embodiment provides a delayed and sustained release composition wherein the tablet further comprises a coating of a water-insoluble polymer.

A preferred embodiment provides a delayed and sustained release composition wherein less than 15% by weight of the energy molecule is released within 2 hours after administration in a simulated gastric fluid dissolution media; the energy molecule being released at a sustained rate after 2 hours, wherein less than 60% by weight of the energy molecule is released within the first 4 hours and at least 85% by weight of the energy molecule is released within 8 hours after administration in a simulated intestinal fluid dissolution media using USP dissolution method II at 50 rpm.

A further embodiment provides a delayed and sustained release composition wherein the pH-dependent polymer is selected from the group consisting of: a polyacrylate material, a cellulose acetate phthalate, cellulose phthalate hydroxy propyl methyl ether, polyvinyl acetate phthalate, hydroxy propyl methyl cellulose acetate succinate, cellulose acetate trimellitate, and shellac.

A further embodiment provides a delayed and sustained release composition wherein the hydrophilic polymer is selected from the group consisting of: hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose, the hydrophilic polymer having a viscosity within the range of from about 60 to about 7,000,000 centipoises in a 2% by weight water solution at 25 degrees Celsius, as measured by a Brookfield LV viscometer.

A further embodiment provides a delayed and sustained release composition wherein the water-insoluble polymer is selected from the group consisting of: ethyl cellulose, acetate cellulose, and polyacrylate copolymer.

A further embodiment of the present invention provides a method for treating nocturnal hypoglycemia comprising administering to a subject in need thereof, the composition of claim 1 immediately prior to going to sleep.

A further embodiment of the present invention provides a transdermal delivery device comprising: a reservoir layer comprising absorbent materials inert to chemicals, the reservoir layer containing a composition comprising an energy molecule required for human brain function and a skin permeation enhancer formulation; an adhesive layer attached to the reservoir layer and configured to secure the device to the skin and seal it so as to prevent leaking; a backing layer coated by the adhesive layer and impermeable by the energy molecules and the enhancer mixture; a release liner that is inert to chemicals and protects the adhesive layer and the reservoir layer before being peeled off for administration, and configured to release the composition contained in the reservoir layer such that less than 10% by weight of the energy molecule is delivered to blood circulation within 2 hours after administration, the energy molecule being delivered at a sustained rate after 2 hours for a period of time up to at least 8 hours.

A further embodiment of the transdermal delivery device provides wherein the backing layer is impermeable to the energy molecules and the energy molecule is one or more molecules selected from the group consisting of: glucose, mannose, lactic acid (lactate), and pyruvic acid (pyruvate).

A further embodiment of the present invention provides a method for treating a subject having nocturnal hypoglycemia comprising placing the transdermal device on the subject's neck area proximate to the subject's carotid artery immediately prior to going to sleep.

A further embodiment provides a method wherein the device is configured to load the composition of energy molecule and enhancer mixture into the reservoir layer after detaching the release liner and before applying the device to the skin.

A further embodiment provides a method wherein the energy molecule is one or more molecules selected from the group consisting of: glucose, mannose, lactic acid (lactate), and pyruvic acid (pyruvate).

DETAILED DESCRIPTION OF THE INVENTION

Embodiments and applications of the invention presented here are described below. Unless specifically noted, it is intended that the words and phrases in the specification and the claims be given their plain, ordinary, and accustomed meaning to those of ordinary skill in the applicable arts.

A preferred embodiment of a delayed and sustained release composition comprises an energy molecule required for human brain function. Energy molecules required for human brain function include molecules which do not require further digestion or enzymatic break down by the human body and are utilized by the human brain for energy support. In one embodiment, the energy molecule is glucose. In another embodiment the energy molecule is typically mannose, lactic acid (lactate) or pyruvic acid (pyruvate). In yet another embodiment the composition comprises a combination of two of these energy molecules.

The delayed and sustained release composition is configured to release less than 15% (e.g., less than 10%, 5%, and 2%), by weight, of the energy molecule within 2 hours after administration. After 2 hours, the energy molecule is preferably released at a sustained rate such that less than 60% (e.g., less than 55%, 50%, 40%), by weight of the energy molecule is released within the first 4 hours of administration, and at least 80% (e.g., at least 85%, 90%, or 95%), by weight, of the energy molecule is released within 8 hours after administration. In a more preferred embodiment, less than 5%, by weight, of the energy molecule is released within 2 hours after administration, less than 55% of the energy molecule is released within the first 4 hours and at least 85%, by weight, of the energy molecule is released within 8 hours after administration.

The delayed and sustained release composition preferably comprises a transdermal preparation for certain transdermal embodiments. The transdermal preparation typically includes a skin permeation enhancer formulation. A preferred embodiment of skin permeation enhancer formulation comprises at least one glycol, monothioglycerol, at least one of 2-methyl-3-hydroxypyranone or 2-ethyl-3-hydroxypyranone and an aliphatic carboxylic acid of 8 to 24 carbon atoms or an ester of said acid with an aliphatic alcohol of 1 to 14 carbon atoms and 1 to 2 hydroxy groups. In a more preferred embodiment, the skin permeation enhancer formulation has a composition of 10% to 95%, by weight, of the at least one glycol, 1% to 10%, by weight, of monothioglycerol, 2% to 30%, by weight, of the at least one of 2-methyl-3-hydroxypyranone or 2-ethyl-3-hydroxypyranone and 2%-10%, by weight, of the aliphatic carboxylic acid of 8 to 24 carbon atoms or an ester of said acid with an aliphatic alcohol of 1 to 14 carbon atoms and 1 to 2 hydroxy groups. The at least one glycol is typically selected from the group consisting of propylene glycol, butylenes glycol, hexylene glycol, ethoxydiglycol, dipropylene glycol and pentylene glycol. In a preferred embodiment, the skin permeation enhancer formulation has a composition of about 70-80%, by weight, butylene glycol, about 3-9%, by weight, monothioglycerol, about 10%, by weight, 2-methyl 3-hydroxy pyranones and about 4-12%, by weight, oleic acid. In a most preferred embodiment, the skin permeation enhancer formulation has a composition of about 76%, by weight, butylene glycol, about 6%, by weight, monothioglycerol, about 10%, by weight, 2-methyl 3-hydroxy pyranones and about 8%, by weight, oleic acid.

In certain embodiments, the delayed and sustained release composition is an oral tablet. The oral tablets preferably contains between about 250 milligrams and about 1250 milligrams of an energy molecule. In a more preferred embodiment, the oral tablet contains between about 500 milligrams and about 1000 milligrams of an energy molecule. In a most preferred embodiment, the oral tablet contains about 750 milligrams of an energy molecule. Other amounts of the energy molecule may also be contained in the oral tablet. Preferably, the tablets are designed to suitable sizes or compositions based on the age or physical characteristics of the patient as well as the severity of the disease.

Other suitable oral dosage forms include capsules and caplets. Preferred oral capsules contain between about 250 milligrams and about 1250 milligrams of an energy molecule. In a more preferred embodiment, the oral capsule contains between about 500 milligrams and about 1000 milligrams of an energy molecule. In a most preferred embodiment, the oral capsule contains about 750 milligrams of an energy molecule. Other amounts of the energy molecule may also be contained in the oral capsules.

Preferably, the capsules are designed to suitable sizes or compositions based on the age or physical characteristics of the patient as well as the severity of the disease. Such dosage forms are prepared using conventional methods known to those in the field of pharmaceutical formulation and described in the pertinent texts, (e.g., Remington: The Science and Practice of Pharmacy, Twentieth Ed. (Philadelphia, Pa.: Lippincott Williams & Wilkins, 2000)). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In those embodiments, wherein the dosage form is a capsule, the brain energy molecule-containing composition is typically encapsulated in the form of a solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals.

Preferred solid dosage forms, whether tablets, capsules, caplets, or particulates, are preferably coated or have a coating so as to provide for delayed and sustained release. Dosage forms with delayed and sustained release coatings may be manufactured using standard coating procedures and equipment. (See, for e.g., Remington: The Science and Practice of Pharmacy, supra).

In a preferred embodiment, the oral tablet or capsules comprise a coating of a pH-dependent polymer. The pH-dependent polymer is preferably selected from the group consisting of: a polyacrylate material, a cellulose acetate phthalate, cellulose phthalate hydroxyl propyl methyl ether, polyvinyl acetate phthalate, hydroxyl propyl methyl cellulose acetate succinate, cellulose acetate trimellitate and shellac. In another preferred embodiment, the oral tablet further comprises a hydrophilic polymer. The hydrophilic polymer is preferably selected from the group consisting of: hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose. The hydrophilic polymer preferably has a viscosity within the range of from about 60 to about 7,000,000 centipoises in a 2% by weight water solution at 25 degrees Celsius, as measured by a Brookfield LV viscometer. In another preferred embodiment, the oral tablet further comprises a water-insoluble polymer. The water-insoluble polymer is preferably selected from the group consisting of: ethyl cellulose, acetate cellulose and polyacrylate copolymer. The coatings provide for the delayed and the sustained release of the energy molecules.

One embodiment of the invention provides a method for treating nocturnal hypoglycemia. The method typically comprises administering the delayed and sustained release composition comprising the energy molecule to a subject in need thereof, immediately prior to going to sleep. In a preferred embodiment, the composition does not contain digestible substances thereby allowing the sleep cycle of the subject to not be disturbed while allowing subject to still receive the energy molecule required for human brain function. The method may also be useful for treating Alzheimer's disease and other CNS diseases.

Another embodiment of the invention provides a transdermal delivery device. The transdermal delivery device preferably comprises a reservoir layer, an adhesive layer, a backing layer and a release liner. The reservoir layer typically comprises absorbent materials inert to chemicals and preferably contains a composition comprising an energy molecule and a skin permeation enhancer formulation. In one embodiment, the reservoir layer is typically loaded up to saturation or super saturation with energy molecules to allow a high thermodynamic activity of the energy molecules.

In a preferred embodiment, the skin permeation enhancer formulation is the formulation described above. Other skin permeation enhancer formulations may also be used.

The adhesive layer is typically attached to the reservoir layer to secure and seal the device to the skin to prevent leaking. In order to allow the adhesive layer to secure and seal the device to the skin, the adhesive layer preferably has margins that extend farther than the reservoir layer to prevent leaking when the device is in use. Preferably, the backing layer is coated by the adhesive layer and, in a preferred embodiment, is impermeable to the energy molecule. In a preferred embodiment, the release liner is inert to chemicals and is configured to release the composition contained in the reservoir layer such that less than 10% (e.g., less than 5%) by weight of the energy molecule is released within 2 hours after administration, the energy molecule being released at a sustained rate after 2 hours for 8 hours or more.

The energy molecule used in the transdermal delivery device is the same as is found in the oral tablet. The energy molecule is typically one or more molecules selected from the group consisting of: glucose, mannose, lactic acid (lactate), and pyruvic acid (pyruvate).

The backing layer preferably comprises any material that is impermeable for the energy molecules and physically and chemically stable to the skin permeation enhancer formulation. In a preferred embodiment, the backing layer is comprised of a commercially available material, such as SCOTCHPAK by 3M, though other materials may be utilized. In other embodiments, the adhesive layer is coated to the backing and provides attachment for the reservoir and also surrounds and seals the reservoir onto the skin. The adhesive layer typically comprises any adhesive material that is physically and chemically compatible with the reservoir layer. In a preferred embodiment, the adhesive layer comprises EUDRAGIT acrylic adhesives. In another embodiment, the adhesive layer comprises NATIONAL STARCH acrylic adhesives. Other suitable adhesives may be used as well.

The reservoir layer typically comprises any absorbent material inert to the energy molecules and the skin permeation enhancer formulation. The absorbent material is fixed to the transdermal delivery device through adhesion to the adhesive layer on the backing layer. In a preferred embodiment, cotton fabric is utilized as the absorbent material. In another embodiment, polypropylene non-woven material is utilized as the absorbent material. Other absorbent materials may also be utilized in addition to these two options.

One embodiment of the invention provides a method for treating a subject having nocturnal hypoglycemia through use of the transdermal delivery device. In a preferred embodiment, the transdermal delivery device is placed anywhere on the subject's skin immediately prior to going to sleep. In a more preferred embodiment, the transdermal delivery device is placed anywhere on the subject's neck immediately prior to going to sleep. In a most preferred embodiment, the transdermal delivery device is placed on the subject's neck area proximate to the subject's carotid artery immediately prior to going to sleep.

In a preferred implementation of this method, the device is configured to load the composition into the reservoir layer after detaching the release liner and before applying the device to the skin. In such an embodiment, there may be a kit utilized which comprises a transdermal delivery device and a bottle of a composition comprising the energy molecule and skin permeation enhancer formulation. A subject detaches the release liner, fills the reservoir layer with the composition from the bottle, and then applies the device to the subject's neck proximate to the subject's carotid artery. In another implementation of this method, the reservoir layer is preloaded with the liquid mixture of energy molecules and enhancers.

EXAMPLES

The following compositions, provided by way of example and not limitation, are related to a delayed and sustained release of energy molecules useful for brain function.

Example 1

An oral composition comprising 750 mg of glucose, 75 mg of hydroxyl ethyl cellulose and other conventional pharmaceutical ingredients, such as Magnesium Stearate as a lubricant. This composition is first granulated and then compressed into core tablets.

The core tablets are spray coated with polyacrylated copolymer aqueous solution (EUDRAGIT® NE 30 D). Finally, the tablets are coated with cellulose acetate phthalate (Aquacoat® CPD Cellulose Acetate Phthalate Aqueous Dispersion).

Example 2

A transdermal delivery device with a skin permeation enhancer formulation of:
  76% Butylene Glycol, by weight,
  6% monothioglycerol, by weight,
  10% 2-methyl 3-Hydroxy Pyranones, by weight, and
  8% Oleic Acid, by weight.

A suspension of enhancer mixture with a saturated energy molecule of Lactic acid was added to the Franz cell donor compartment, while the receiver compartment on the other side of skin contained PH 7.4 isotonic solution. The permeation test set was carried out at constant temperature of 32 degree C. for a period of 10 hours.

Example 3

Testing of a preferred embodiment for the oral formulations was carried out using USP dissolution method II. USP dissolution method II is well known in the art and is described in chapter 711 of Stage 6 Harmonization of The United States Pharmacopeia and The National Formulary, which is incorporated herein by reference. The preferred embodiment was tested using USP dissolution method II in a simulated gastric fluid dissolution media at 50 revolutions per minute for two hours, rinsed, and followed immediately after rinsing by testing in a simulated intestinal fluid dissolution media at 50 revolutions per minute for an extended period of time. Testing revealed that less than 5% of the energy molecule being released within 2 hours in the gastric fluid after administration, less than 60% of the energy molecule within the first 4 hours and at least 85% of the energy molecule being released within 8 hours after administration.

Having herein set forth various embodiments of the present invention, it is anticipated that suitable modifications can be made thereto which will nonetheless remain within the scope of the invention. The invention shall therefore only be construed in accordance with the following claims below.

What is claimed is:

1. A delayed and sustained release oral tablet or capsule comprising:

a core tablet, the core tablet comprising:
  an energy molecule required for human brain function in an amount between about 750 milligrams and about 1250 milligrams, the energy molecule being selected from the group consisting of: glucose, mannose, lactic acid, and pyruvic acid; and
  a hydrophilic polymer;
a water-insoluble polymer coating, wherein the water-insoluble polymer coating is applied to the core tablet; and
a pH-dependent polymer coating, wherein the pH-dependent polymer coating is applied to the core tablet coated with the water-insoluble polymer coating,
the delayed and sustained release oral tablet or capsule being configured to release less than 15% by weight of the energy molecule in the core tablet within 2 hours after administration; after 2 hours, the delayed and sustained release oral tablet or capsule being configured to release the energy molecule at a sustained rate with less than 60% of the energy molecule being released within the first 4 hours; and further configured to release at a sustained rate at least 80% of the energy molecule within 8 hours after oral administration.

2. The delayed and sustained release oral tablet or capsule of claim 1 configured to release less than 5% by weight of the energy molecule in the core tablet within 2 hours after administration, less than 60% by weight of the energy molecule being released within the first 4 hours and at least 85% by weight of the energy molecule being released at a sustained rate within 8 hours after administration.

3. The delayed and sustained release oral tablet or capsule of claim 1, wherein the energy molecule is glucose.

4. The delayed and sustained release oral tablet or capsule of claim 1, wherein the pH-dependent polymer is selected from the group consisting of: a polyacrylate material, a cellulose acetate phthalate, cellulose phthalate hydroxy propyl methyl ether, polyvinyl acetate phthalate, hydroxy propyl methyl cellulose acetate succinate, cellulose acetate trimellitate, and shellac.

5. The delayed and sustained release oral tablet or capsule of claim 1, wherein the hydrophilic polymer is selected from the group consisting of: hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose.

6. The delayed and sustained release oral tablet or capsule of claim 1, wherein the water-insoluble polymer is selected from the group consisting of: ethyl cellulose, acetate cellulose, and polyacrylate copolymer, wherein the water-insoluble polymer coating is applied to the core tablet.

7. The delayed and sustained release oral tablet or capsule of claim 1 configured so that less than 15% by weight of the energy molecule in the core tablet is released within 2 hours after administration in a simulated gastric fluid dissolution media, the energy molecule is released at a sustained rate with less than 60% by weight of the energy molecule released within the first 4 hours and at least 85% by weight of the energy molecule released within 8 hours after administration in a simulated intestinal fluid dissolution media using USP dissolution method II at 50 rpm.

8. The delayed and sustained release oral tablet or capsule of claim 5, wherein the hydrophilic polymer has a viscosity within the range of from about 60 to about 7,000,000 centipoises in a 2% by weight water solution at 25 degrees Celsius, as measured by a Brookfield LV viscometer.

9. The delayed and sustained release oral tablet or capsule of claim 7, wherein the energy molecule is glucose.

* * * * *